(12) United States Patent
Boudreaux et al.

(10) Patent No.: US 10,701,930 B2
(45) Date of Patent: Jul. 7, 2020

(54) COMPOSITIONS AND METHODS FOR TREATING WATER BY STABILIZING AN OXIDIZING BIOCIDE

(71) Applicant: CHEMTREAT, INC., Glen Allen, VA (US)

(72) Inventors: Kevin Boudreaux, Cincinatti, OH (US); Prasad Kalakodimi, Richmond, VA (US); Douglas Mcilwaine, Ashland, VA (US); Saarika Koneru, Richmond, VA (US)

(73) Assignee: CHEMTREAT, INC., Glen Allen, VA (US)

( * ) Notice: Subject to any disclaimer, the term of this patent is extended or adjusted under 35 U.S.C. 154(b) by 134 days.

(21) Appl. No.: 15/792,079

(22) Filed: Oct. 24, 2017

(65) Prior Publication Data
US 2019/0116787 A1 Apr. 25, 2019

(51) Int. Cl.
| | | |
|---|---|---|
| *A01N 25/22* | (2006.01) | |
| *A61L 2/16* | (2006.01) | |
| *C02F 1/76* | (2006.01) | |
| *C02F 1/50* | (2006.01) | |
| *A01N 59/00* | (2006.01) | |
| *A01N 43/50* | (2006.01) | |
| *A01N 25/30* | (2006.01) | |
| *C02F 1/00* | (2006.01) | |
| *C02F 103/02* | (2006.01) | |

(52) U.S. Cl.
CPC ............. *A01N 25/22* (2013.01); *A01N 25/30* (2013.01); *A01N 43/50* (2013.01); *A01N 59/00* (2013.01); *A61L 2/16* (2013.01); *C02F 1/00* (2013.01); *C02F 1/50* (2013.01); *C02F 1/76* (2013.01); *C02F 2103/023* (2013.01); *C02F 2303/04* (2013.01); *C02F 2303/20* (2013.01); *C02F 2305/04* (2013.01)

(58) Field of Classification Search
None
See application file for complete search history.

(56) References Cited

U.S. PATENT DOCUMENTS

| | | | | |
|---|---|---|---|---|
| 6,471,974 | B1 * | 10/2002 | Rees ..................... | A01N 59/00 |
| | | | | 252/187.25 |
| 2002/0056689 | A1 * | 5/2002 | Shim ..................... | A01N 59/00 |
| | | | | 210/756 |
| 2006/0049119 | A1 * | 3/2006 | Ludensky ............. | A01N 59/00 |
| | | | | 210/755 |
| 2008/0108537 | A1 * | 5/2008 | Rees ..................... | A01N 59/00 |
| | | | | 510/258 |

FOREIGN PATENT DOCUMENTS

FR 2332763 A1 * 6/1977 ............. A01N 43/50

OTHER PUBLICATIONS

Machine translation of FR2332763, pp. 1-7. (Year: 1976).*

* cited by examiner

*Primary Examiner* — Clare M Perrin
(74) *Attorney, Agent, or Firm* — Oliff PLC

(57) ABSTRACT

Methods and liquid compositions for stabilizing an oxidizing biocide in a water system. The liquid composition comprises a hydantoin, and a surfactant, a ratio of a concentration of the hydantoin to the surfactant in the liquid composition is in a range of 1:1 to 99:1 by volume. The method comprises mixing a hydantoin, a surfactant and an oxidizing biocide with water to form a liquid treatment composition, and then adding the liquid treatment composition to a water stream in the water system, the liquid treatment composition improving the efficacy of the oxidizing biocide in the water stream.

10 Claims, No Drawings

COMPOSITIONS AND METHODS FOR TREATING WATER BY STABILIZING AN OXIDIZING BIOCIDE

TECHNICAL FIELD

This application is directed to compositions and methods for treating water by stabilizing and increasing the efficacy of an oxidizing biocide in water systems.

BACKGROUND

Biofouling is a detrimental type of fouling experienced in industrial water treatment applications. Regardless of industry, water treatment experts spend a considerable amount of their time focused on preventing biofouling of heat exchangers and cooling towers. When biofouled, poorly performing heat exchangers and cooling towers can lead to millions of dollars in lost revenues.

The use of oxidizing and non-oxidizing biocides for microbiological control in industrial applications is known. However, the known chemistries have significant drawbacks when it comes to overall efficacy, safety, and delivery.

Methods for combining stabilizers with oxidizing biocides vary, but include: (i) direct injection of the stabilizer into a biocide such as hypochlorite, which is then injected into an aqueous system, (ii) injection of the stabilizing component and biocide such as hypochlorite into the aqueous system separately but in close proximity, and (iii) creating a solid form of a stabilized product, which is then dissolved into an aqueous system.

Whether stabilized or not, oxidizing biocides have difficulty penetrating biofilms once they have been established. While it is possible to feed an exorbitant amount of oxidizing biocide to essentially "burn" the system, the high levels of free oxidant increase corrosion rates throughout the water system. To help improve the oxidizing biocide's ability to penetrate these films and make contact with the microorganisms, biosurfactants have been implemented.

Biosurfactants, sometimes referred to as biodispersants, significantly improve the efficacy of both oxidizing and non-oxidizing biocides. There are subtle differences between biosurfactants and biodispersants, but they have the same function—minimize the growth and adherence of biofilms. Biosurfactants work by actually removing the biofilm in a scrubbing type action, while biodispersants disperse bio matter so that it cannot agglomerate.

Research has shown that biofilms are typically 30 to 40% organic matter, with the rest being inorganic material such as silt, metals, and other particulate matter. Other dispersants, such as sulfonated polymers and copolymers, are sometimes used in conjunction with biodispersants and biosurfactants to help disperse these inorganic materials. While this approach can be effective, it involves a comprehensive and cumbersome water chemistry program.

Conventional efforts have attempted to address these issues by combining stabilizer, surfactant, and a halide ion in a solid form. However, practical application of the solid form in water systems requires special feed systems such as pot feeders and requires manual handling of the chemicals. Other programs have been developed that generate stabilized oxidizing biocides. For example, researchers have combined a stabilizer and a bromine source into a single chemistry, as well as combined a bromine and surfactant into a single chemistry. But these programs require expensive generators, and may pose significant hazards if the systems fail.

SUMMARY

It is an object of the disclosed embodiments to provide unique compositions and methods employing a stabilizer compound and a surfactant in a convenient single liquid chemistry that increases the stability and efficacy of an oxidizing biocide. Disclosed methods allow for the dual benefit of stabilizing an oxidizing biocide, while simultaneously including a surfactant to improve biofilm removal and penetration. This results in surprisingly lower biocide requirements, less halogenated organics such as trihalomethanes (THM's) and adsorbable organic halides (AOX's), better photostability, and cleaner heat transfer surfaces. Furthermore, a stabilized halogen is less susceptible to gas-off across the cooling tower Additional benefits of the disclosed compositions and methods in comparison to conventional programs include: (1) reduced halogen decomposition due to organics, (2) reduced predisposition of AOX formation, (3) provision of a non-biocidal stabilizer/surfactant blended chemistry, thereby eliminating hazards typically associated with biocide chemistries, (4) improved biofilm removal, thereby allowing halogens to effectively reach microorganisms, (5) more persistent stabilized chemistry, thereby reducing overall biocide feed rates, and thus environmental impact, and (6) safe in situ production that does not require generation equipment.

DETAILED DESCRIPTION

The disclosed embodiments provide a stabilizer compound and a surfactant that are combined to form a stable liquid composition and methods for adding an oxidizing biocide in situ at the point of application. Conventional methods of treatment require special generation devices to create a stabilized halogen. The methods disclosed herein avoid these drawbacks by providing a particular hydantoin/ surfactant liquid formulation that does not have any biocidal properties by itself, and therefore is non-hazardous to transport and handle, as well as environmentally friendly.

The usage and handling of commercial oxidizing biocides are generally governed by the Environmental Protection Agency's (EPA) Toxic Substances Control Act (TSCA). As will be understood by one of ordinary skill in the art, any suitable oxidizing biocide within acceptable EPA-designated concentrations are contemplated by this disclosure. For example, in embodiments, the oxidizing biocide may sodium hypochlorite (NaOCl) (bleach), chlorine gas ($Cl_2$), and bleaching powder or calcium hypochlorite ($Ca(OCl)_2$). The concentration of oxidizing biocide contemplated by this disclosure is also not particularly limited. For purposes of this disclosure, the oxidizing biocide will be described with reference to industrial bleach or sodium hypochlorite which may be in the range of 10% to 20% solution, and usually 12%, user-dilution notwithstanding.

Formulation

In embodiments, the preferred formulation is a mixture of a bleach stabilizing compound and a surfactant that increases the efficacy of bleach as an oxidizing biocide. Given that bleach is heavily regulated as a toxic substance under EPA regulations, it is costly to handle and transport.

Therefore, in embodiments, the stabilizer and surfactant are pre-mixed in a liquid composition and transported to the water system to be mixed with the bleach in situ. The stabilizer/surfactant blended chemistry is non-biocidal, thereby eliminating hazards typically associated with transporting and handling conventional biocide chemistries.

According to embodiments, the preferred stabilizer is a hydantoin compound such as, for example, an unhalogentaed alkyl hydantoin. An unhalogentaed alkyl hydantoin is a heterocyclic organic compound the general structure of which is illustrated below.

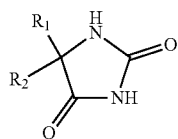

In the above structure, $R_1$ and $R_2$ are selected from H, $CH_3$, $C_2H_5$, or $C_3H_7$. Preferably, $R_1$ and $R_2$ are both $CH_3$.

Hydantoin is a colorless solid that arises from the reaction of glycolic acid and urea. It is an oxidized derivative of imidazolidine. The inventors have found that an unhalogentaed alkyl hydantoin compound is uniquely suited to "stabilize" the oxidizing biocide by the formation of biocidal byproducts such as chloramines through a known reaction of hydantoin with bleach. Chloramines may include, but are not limited to, monochloramine, dichloramine, and organic chloramines. Chloramines provide long-lasting protection and are more stable than pure chlorine products as they do not break down as quickly in water systems. It is known that in the absence of a stabilizer compound, bleach rapidly and almost completely oxides into chloride.

The inventors have found that only a select class of surfactants exhibit the requisite stability in the presence of industrial bleach so as to maintain its functionality as a biodispersant. In this regard, industrial bleach is known to oxidize most surfactants along with target biofilms in water treatment systems. Any surfactant that exhibits stability with bleach would generally be considered suitable for use in the disclosed methods and formulations. For example, the surfactant may be, but is not limited to, any one or more of the following: linear alkylbenzene sulfonate, sodium lauryl sulfoacetate, disodium lauryl sulfosuccinate, sodium dioctyl sulfosuccinate, alkyl polyglycoside, sodium dodecylbenzene sulfonate, nonionic polyoxyethylene, polyoxypropylene block copolymer, ethoxylated alkyl phenol nonionic surfactant, glucoside, terpene-based proprietary dispersant, ethylene oxide/propylene oxide alcohols, polyoxyethylene ether, sodium dodecyl diphenyloxide disulfonate and mixtures thereof. Preferably, the surfactant is an alkyl polyglycoside or ethylene oxide/propylene oxide alcohols. The inventors have found that alkyl polyglycoside and ethylene oxide/propylene oxide alcohols exhibit particularly unexpected stability in the presence of industrial bleach.

In disclosed embodiments, a suitable ratio of concentration of the stabilizer to the surfactant in the liquid composition is in a range of 1:1 to 99:1 by volume, preferably 9:1 to 99:1 by volume, and more preferably 19:1 to 99:1 by volume.

In embodiments, an optional halide ion source may also be added to the stabilizer/surfactant liquid composition. The optional halide ion source may include, but is not limited to, ammonium bromide, sodium bromide, calcium bromide, potassium bromide, sodium iodide, calcium iodide, and potassium iodide and mixtures thereof.

In disclosed embodiments, a suitable ratio of concentration of the halide ion source to the hydantoin in the liquid composition is in a range of 0.001:1 to 20:1, preferably 0.1:1 to 10:1, and more preferably 0.05:1 to 4:1 by volume.

Methods of Treatment

According to embodiments, the method for stabilizing an oxidizing biocide in a water system may include mixing the hydantoin and the surfactant with water to form the liquid composition according to the formulation described above. Then, this liquid composition can be mixed with the oxidizing biocide to form a liquid treatment composition and the liquid treatment composition is added to a water stream in the water system, such that the liquid composition treatment improves the efficacy of the oxidizing biocide in the water stream.

In embodiments, mixing the liquid composition with the oxidizing biocide may include mixing the liquid composition with the oxidizing biocide in situ to form the liquid treatment composition, and adding the liquid treatment composition to the water stream in the water system may include injecting the liquid treatment composition into the water stream of the water system. Mixing the liquid composition with the oxidizing biocide may include mixing the liquid composition with the oxidizing biocide separately into a carry water solution to form the liquid treatment composition, and adding the liquid treatment composition to the water stream in the water system may include injecting the carry water solution into the water stream of the water system.

The blending of the stabilizer/surfactant liquid composition and oxidizing biocide can be accomplished by direct injection of the oxidizing biocide into the liquid composition. This blending may be done by in-line feeding or direct injection of the oxidizing biocide and the liquid composition separately into carry-water. Once blended, the liquid treatment composition is added to a water system via a continuous drip feed or slug feed process. This method of applying the unique stabilizer/surfactant liquid chemistry with the bleach in situ provides a safe and effective means of delivering an effective biocide program without the use of expensive, complicated generating systems.

According to embodiments, a suitable ratio of the concentration of the industrial bleach to the hydantoin in solution at the point of application is in a range of 0.2:1 to 8:1 by volume, preferably 1:1 to 5:1 by volume, and more preferably 1:1 to 3:1 by volume.

The liquid treatment composition including the stabilizer/surfactant liquid composition and industrial bleach may be added to the water stream in the feed line or carry-water at a concentration in a range of 0.05 mg/L to 1,000 mg/L or 0.1 to 300 mg/L, preferably 1 to 10 mg/L, and more preferably 0.5 to 5 mg/L, relative to all components in the water stream.

The water system may include, but is not limited to, cooling water systems, cooling towers, surface condensers, scrubbers, heat exchangers, air washers, evaporative condensers, once-through cooling water systems, paper mill water systems, reverse osmosis system feedwaters and brewery pasteurizers.

It will be appreciated that the above-disclosed features and functions, or alternatives thereof, may be desirably combined into different systems or methods. Also, various alternatives, modifications, variations or improvements may be subsequently made by those skilled in the art. As such, various changes may be made without departing from the spirit and scope of this disclosure.

What is claimed is:

1. A method for stabilizing an oxidizing biocide, the method comprising:
   mixing an unhalogenated hydantoin and a surfactant with water to form a liquid treatment composition; and
   then adding a mixture of the liquid treatment composition and an oxidizing biocide to a water stream in a water system, the liquid treatment composition improving the efficacy of the oxidizing biocide in the water stream,
   wherein the oxidizing biocide is selected from the group consisting of calcium hypochlorite, chlorine gas and sodium hypochlorite.

2. The method for stabilizing an oxidizing biocide according to claim 1, wherein the oxidizing biocide is sodium hypochlorite.

3. The method for stabilizing an oxidizing biocide according to claim 1, wherein a ratio of a concentration of the oxidizing biocide to the hydantoin in the mixture is in a range of 0.2:1 to 8:1 by volume.

4. The method for stabilizing an oxidizing biocide according to claim 1, wherein a ratio of a concentration of the oxidizing biocide to the hydantoin in the mixture is in a range of 1:1 to 5:1 by volume.

5. The method for stabilizing an oxidizing biocide according to claim 1, wherein a ratio of a concentration of the oxidizing biocide to the hydantoin in the mixture is in a range of 1:1 to 3:1 by volume.

6. The method for stabilizing an oxidizing biocide according to claim 1, wherein adding the mixture of the liquid treatment composition and the oxidizing biocide includes injecting the mixture into the water stream of the water system.

7. The method for stabilizing an oxidizing biocide according to claim 1, wherein adding the mixture of the liquid treatment composition and the oxidizing biocide to the water stream in the water system includes mixing the liquid treatment composition with the oxidizing biocide into a secondary water solution to form a second mixture, and injecting the second mixture into the water stream of the water system.

8. The method for stabilizing an oxidizing biocide according to claim 1, wherein the mixture is added to the water stream in the water system at a concentration in a range of 0.1 mg/L to 300 mg/L.

9. The method for stabilizing an oxidizing biocide according to claim 1, wherein the water system is selected from the group consisting of cooling water systems, cooling towers, surface condensers, scrubbers, heat exchangers, air washers, evaporative condensers, once-through cooling water systems, paper mill water systems, reverse osmosis system feedwaters and brewery pasteurizers.

10. The method for stabilizing an oxidizing biocide according to claim 1, wherein the mixture of the liquid treatment composition and the oxidizing biocide are added to the water stream in amounts sufficient to establish an effective biocide.

* * * * *